US006433356B1

United States Patent
Cahen et al.

(10) Patent No.: US 6,433,356 B1
(45) Date of Patent: Aug. 13, 2002

(54) HYBRID ORGANIC-INORGANIC SEMICONDUCTOR STRUCTURES AND SENSORS BASED THEREON

(75) Inventors: David Cahen; Konstantin Gartsman; Alexander Kadyshevitch, all of Rehovot; Ron Naaman, Nes-Ziona; Abraham Shanzer, Rehovot, all of (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/297,303

(22) PCT Filed: Oct. 29, 1997

(86) PCT No.: PCT/IL97/00348

§ 371 (c)(1), (2), (4) Date: Jul. 14, 1999

(87) PCT Pub. No.: WO98/19151

PCT Pub. Date: May 7, 1998

(30) Foreign Application Priority Data

Oct. 29, 1996 (IL) .................................................. 119514

(51) Int. Cl.[7] .............................................. H01L 51/00
(52) U.S. Cl. .......................... 257/40; 257/184; 257/194; 257/253; 257/414
(58) Field of Search .......................... 257/40, 194, 184, 257/253, 414

(56) References Cited

U.S. PATENT DOCUMENTS

| 3,781,748 A | 12/1973 | Bishop et al. |
| 3,831,432 A | 8/1974 | Cox |
| 4,777,019 A | 10/1988 | Dandekar |
| 5,854,139 A | * 12/1998 | Aratani et al. ............... 438/780 |

FOREIGN PATENT DOCUMENTS

WO    WO 96/09534    3/1996

OTHER PUBLICATIONS

Besser et al, "Effect of sodium sulfide treatment on band bending in GaAs", *Appl. Phys. Lett.* 52:1707–1709 (1988).

(List continued on next page.)

*Primary Examiner*—Jerome Jackson, Jr.
*Assistant Examiner*—N. Drew Richards
(74) *Attorney, Agent, or Firm*—Browdy and Neimark

(57) ABSTRACT

A hybrid organic-inorganic semiconductor device is provided as a sensor for chemicals and light, said device being composed of: (i) at least one layer of a conducting semiconductor such as doped n-GaAs or n-(Al,Ga)As; (ii) at least one insulating layer such as of an undoped semiconductor; e.g. GaAs or (Al,Ga)As; (iii) a thin layer of multifunctional organic sensing molecules directly chemisorbed on one of its surfaces, said multifunctional organic sensing molecules having at least one functional group that binds to said surface and at least one another functional group that serves as a sensor; and (iv) two conducting pads on the top layer making electrical contact with the electrically conducting layer, so that the electrical current can flow between them at a finite distance from the surface of the device. The surface-binding functional group of the multifunctional organic sensing molecule may be one or more aliphatic or aromatic carboxyl, thiol, sulfide, hydroxamic acid or trichlorosilane groups. The functional group that serves as a sensor may be a group suitable for binding and detection of metal ions such as $Cu^{2+}$, $Fe^{2+}$ and $Ru^{2+}$ such as radicals derived from hydroxamic acids, bipyridyl, imidazol and hydroxyquinoline, or a group that is an efficient light absorber at a given wavelength and is suitable for detection of light such as radicals derived from aliphatic or aromatic hydroxamates, substituted aromatic groups such as cyanobenzoyl and methoxybenzoyl, bipyridyl, hydroxyquinoline, or imidazolyl groups to which a metal porphyrin or a metal phtalocyanin residue is attached.

35 Claims, 7 Drawing Sheets-

OTHER PUBLICATIONS

Breuning et al, "Polar Ligand Adsorption Controls Semiconductor Surface Potential", *J. Am. Chem. Soc.* 116:2972–2977 (1994).

Bruening et al, "Controlling the Work Function of CdSe by Chemisorption of Benzoic Acid Derivatives and Chemical Etching", *J. Phys. Chem.* 99:8368–8373 (1995).

Lisensky et al, "Electro–Optical Evidence for the Chelate Effect at Semiconductor Surfaces", *Science* 248:840–843 (1990).

Lunt et al, "Chemical studies of the passivation of GaAs surface recombination using sulfides and thiols", *J. Appl. Phys.* 70(12):7449–7467 (1991).

Mandelis et al, "Pysics, Chemistry, and Technology of Solid State Gas Sensor Devices", vol. 125 in "Chemical Analysis", J. D. Winefordner, ed., John Wiley & Sons, Inc. (New York, 1993), pp. 82–99.

Oh et al, L "Diminution of the surfafce states of GaAs by a sulfur treatment", *J. Appl. Phys.* 76(3):1959–1961 (1994).

O'Reagan et al, "A low–cost, high–efficiency solar cell based on dye–sensitized colloidal $TiO_2$ films", *Nature* 353:737–739 (1991).

Rickert et al, "Self–assembled monolayers for chemical sensors: molecular recognition by immobilized supramolecular structures", *Sensors and Actuators* B 31:45–50 (1996).

Sandroff et al, "Dramatic enhancement in the gain of a GaAs/AlGaAs heterostructure bipolar transistor by surface chemical passivation", *Appl. Phys. Lett.* 51(1):33–35 (1987).

Skromme et al, "Effects of passivating ionic films on the photoluminescence properties of GaAs", *Appl. Phys. Lett.* 51(24):2022–2024 (1987).

Yablonovitch et al, "Nearly ideal electronic properties of sulfide coated GaAs surfaces", *Appl. Phys. Lett.* 51(6):439–441 (1987).

Takai, Toshihiro et al., "A capacitive polymer humidity sensor using silicon substrate.", Technical Digest of the 7th Sensor Symposium, 1998, pp. 185–188.

Assadi, A. et al., "Interaction of planar polymer Schottky barrier diodes with gaseous substances." Sensors and Actuators B, vol. 20, (1994), pp. 71–77.

Lechuga. L.M. et al., "Urea biosensor based on ammonia gas–sensitive Pt/GaAs Schottky diode." Sensors and Actuators B, vol. 21, (1994) pp. 205–208.

Barker, P.S. et al., "Gas sensing using a charge–flow transistor." Sensors and Actuators B, vol. 24–25, (1995), pp. 451–453.

Sze, S.M., "Semiconductor devices—Physics and Technology.", Bell Telephone Laboratories, Inc., (1985), p. 328.

* cited by examiner

HYBRID ORGANIC-INORGANIC SEMICONDUCTOR STRUCTURES AND SENSORS BASED THEREON

CROSS REFERENCE TO RELATED APPLICATION

The present application is the national stage under 35 U.S.C. 371 of PCT/IL97/00348, filed Oct. 29, 1997.

FIELD OF THE INVENTION

The present invention relates to hybrid organic-inorganic semiconductor devices and to sensors for chemicals and light based thereon.

BACKGROUND OF THE INVENTION

Sensors, i.e. devices used to locate or detect chemicals or energy, are measured by their sensitivity and selectivity. The design of sensors is aimed also at achieving robustness and versatility. Combining these qualities in the process of designing a sensor, was proven to be very difficult. The use of organic molecules in sensors has the benefit of versatility and selectivity, but is not associated with robustness, mainly because in many cases electron flow through the organic medium is required thus causing the destruction of the organic medium and therefore limiting the "life time" of sensors of this type.

In those cases where electron flow through the organic medium is not required, sensitivity becomes the limiting parameter. Generally, sensitivity of sensors is proportional to the contact area of the sensitive: surface, because the larger the area the higher the probability that a molecule or photon can be detected by the sensing surface. Thus, in general, sensitivity is assumed to scale with surface area.

The use of semiconductor devices as sensors is known for many years [reviewed by Mandelis and Christofides, 1993]. In general, the presently used semiconductor sensors are based on two schemes: the chemicals are adsorbed either on the gate metal and insulator layers of a field effect transistor (FET) [see, for example, U.S. Pat. No. 4,777,019, Japanese Patent publications Nos. 62163960 and 95107529] or on the surface metal of Schottky diodes.

The electronic properties of a semiconductor surface can be affected by simple chemical treatments [Skromme et al., 1987; Sandroff et al., 1987; Yablonovitch et al., 1987]. The ability to change electronic properties of a semiconductor surface by adsorption of tailor-made organic molecules to achieve selectivity [Rickert et al., 1996] has been demonstrated in the past [Lisensky et al., 1990; O'Regan and Graetzel, 1991; Bruening et al., 1994; Bruening et al., 1995; Lunt et al., 1991]. Thus, combining semiconductors with organic molecules is an attractive option for sensors, as it can combine selectivity and sensitivity. However, whenever organic molecules are involved, robustness remains an issue. In addition, there is a problem of retaining the versatility as the organic molecule needs to be attached in a reproducible and secure manner to the semiconductor.

In applications based on FET-type sensors, at least one of two basic features are found: the first feature is the third electrode (gate) that is located between the two main current-carrying contacts (source and drain) and is used to control the current through the device, in which case the sensor is based on changing the current passing through the device due to adsorption of molecules on the gate [see, for example, U.S. Pat. No. 4,777,019, U.S. Pat. No. 4,992,244, JP 62163960 and JP 95107529]. The other feature is found in the case that an ungated FET is used, a layer is adsorbed between the source and drain, in which case the sensors are characterized by a semiconductor substrate of one conductivity type, having at least two spaced apart regions of opposite conductivity type [U.S. Pat. No. 3,831,432]. These ungated devices suffer from oversensitivity to electrical interference due to their open gate structure, leading to unwanted high noise levels compared to gated devices and explaining the lack of interest in them [see Mandelis and Christofides, 1993].

Earlier proposed FET-based sensors mainly use silicon. This explains the preference for metal-oxide-semiconductor FET (MOSFET)-based structures as the relatively low barrier height that characterizes Si-devices, leads to high leakage currents unless configurations such as MOSFETs are used. An intrinsic problem one faces is the oxidation layer on the surface that reduces the sensitivity to adsorbed chemicals. By adsorbing chemicals directly onto the surface it is possible to achieve higher sensitivity. Contrary to Si, GaAs surfaces do not have a passivating native oxide layer. Hence it is possible to chemically modify the surface states, their charge, and thus the internal field at the space charge layer.

However, one of the main problems with semiconducting GaAs and related materials is that they do not have a stable native oxide film. This well known instability of their surface would seem to exclude their use as sensors because of problems with reproducibility and noise.

The surface states of GaAs are passivated when treated with sulfur (Oh et al., 1994; Besser and Helms, 1988). However, pinning of the Fermi level in GaAs has discouraged their use as chemical-sensitive devices. On the other hand, the special electronic properties of GaAs are eminently suited for the design and fabrication of structures with high electron mobility (i.e. even small changes in carrier concentration become measurable electrically) and in which charge carriers flow at a well-defined distance near the surface. The latter properties can convey onto these structures very high sensitivity to changes in surface potentials.

SUMMARY OF THE INVENTION

It has now been found, in accordance with the present invention, contrary to expectations by those skilled in the art, that it is possible to use unprotected surfaces of GaAs and related materials for the construction of sensors, even after their exposure to ambient, and get stable, sensitive sensing behavior, after special organic molecules are adsorbed on them, these organic molecules both serving as sensors and at the same time stabilizing the properties of the surfaces.

It is an object of the present invention to provide the use of organic molecules that chemisorb in the ambient directly onto specially designed GaAs structures. GaAs was used, notwithstanding its notoriously unstable surface, because a way was developed according to the invention to stabilize the surface in ambient via chemisorption of multifunctional molecules, and because structures using GaAs and (Al,Ga)As can be made extremely sensitive to surface potential changes.

The present invention thus relates to a hybrid organic-inorganic semiconductor device composed of one or more insulating or semi-insulating layers (1), one conducting semiconductor layer (2), two conducting pads (3), and a layer of multifunctional organic molecules (4), characterized in that said conducting semiconductor layer (2) is on top of one of said insulating or semi-insulating layers (1), said two conducting pads (3) are on both sides on top of an upper layer which is either said conducting semiconductor layer (2) or another of said insulating or semi-insulating layers (1), making electrical contact with said conducting semiconductor layer (2), and said layer of multifunctional organic molecules (4) is directly bound through at least one of said functional groups to the surface of said upper layer, between the two conducting pads (3), and at least another of said functional groups of said multifunctional organic molecules binds chemicals or absorbs light.

The multifunctional organic molecule used in the structure of the invention has at least one functional group that binds to the surface of the upper layer, said group being preferably selected from one or more aliphatic or aromatic carboxyl, thiol, sulfide (e.g., methylsulfide, acyclic disulfide, cyclic disulfide), hydroxamic acid and trichlorosilane (for binding to silicon oxide) groups, and at least one second functional group that binds chemicals or absorbs light. Examples of functional groups that bind metal ions and are suitable for detection of metal ions such as $Cu^{2+}$, $Fe^{2+}$, and $Ru^{2+}$, are, without being limited to, radicals derived from hydroxamic acid, bipyridyl, imidazol and hydroxyquinoline. Examples of functional groups that are efficient light absorbers at given wavelenghts and are suitable for detection of light include, without being limited to, aliphatic and aromatic hydroxamates, substituted aromatic groups such as cyanobenzoyl and methoxybenzoyl bipyridyl groups (that can bind $Ru^{2+}$), hydroxyquinoline groups, imidazolyl groups to which a metal porphyrin or a metal phthalocyanin residue is attached, etc.

Examples of multifunctional organic molecules that can be used as light sensors according to the invention are 2,3-di(p-cyanobenzoyl) tartaric acid (DCDC), 4,5-di(p-cyanobenzoyloxy)- 1,2-dithiane (DCDS), 4,5-di(p-methoxy-benzoyloxy)-1,2-dithiane (DMDS) and 1,2-dithiane-4,5-di(hydroxyquinoline) and the $Cu^+$ complex thereof.

The multifunctional organic molecules may further contain functional groups that will control the fundamental properties of the semiconductor surface, such as electron donating or electron withdrawing groups such that a dipole layer with a defined direction is formed on the surface, and/or functional groups that control the sensitivity to certain species, change the hydrophobicity or hydrophilicity of the surface, etc.

In one embodiment, the conducting semiconductor layer (2) of the structure of the invention is a semiconductor selected from a III–V and a II–VI material, or mixtures thereof, wherein III, V, II and VI denote the Periodic Table elements III=Ga, In; V=As, P; II=Cd, Zn; VI=S, Se, Te. This conducting semiconductor material is preferably n-GaAs or n-(Al,Ga)As doped, for example, preferably with Si. In another embodiment, the one or more insulating or semi-insulating layers (1) of a device of the invention, that may serve as the base for the device, is a dielectric material selected from silicon oxide, silicon nitride or from an undoped semiconductor selected from a III–V and a II–VI material, or mixtures thereof, wherein III, V, II and VI denote the Periodic Table elements III=Ga, In; V=As, P; II=Cd, Zn; VI=S, Se, Te, and is preferably an undoped GaAs or (Al, Ga)As substrate.

The invention further provides sensors for chemicals and light based on the devices of the invention.

BRIEF DESCRIPTION OF THE DRAWINGS

In FIG. 3D, the same measurement was performed with the low doped FET-like device of FIG. 2B covered with DCDC. The dotted line presents the curve of the bare device and the solid line corresponds to the signal obtained with the adsorbed organic molecules. The error is ±5%.

DETAILED DESCRIPTION OF THE INVENTION

The present invention will be more fully appreciated from the following detailed description taken in conjunction with the drawings.

Figure 1:
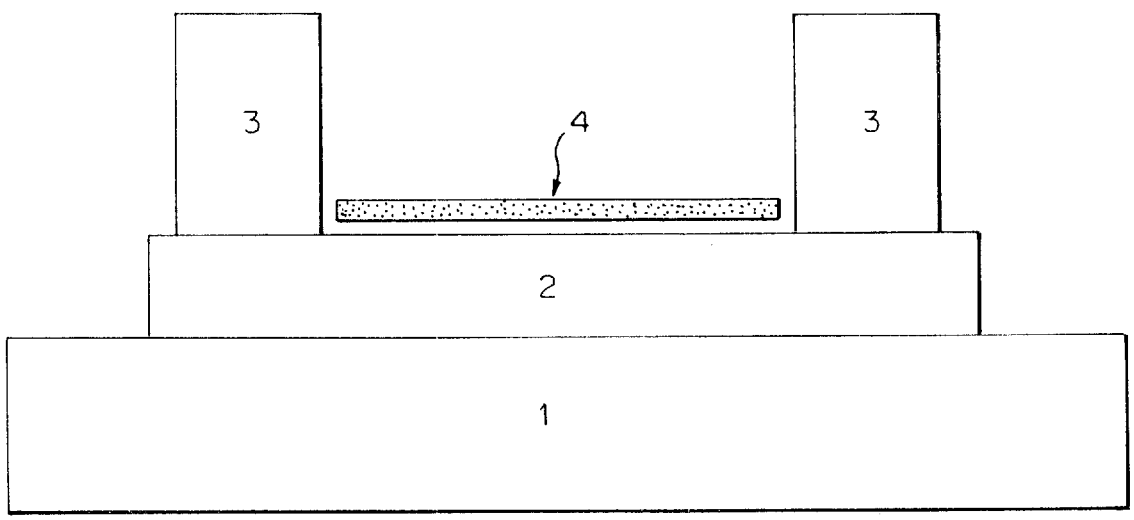
FIG. 1 depicts schematically a hybrid device of the invention.

Reference is now made to FIG. 1, which depicts schematically a sensor device according to the invention in which a undoped, insulating or semi-insulating layer 1 serves as the base for the device, a thin semiconductor layer 2 on top of the base layer is the conductive layer, Ohmic contacts 3 are used as the two current contacts for the device, and on top of the conductive layer 2 a thin film of the multifunctional organic molecules 4 is adsorbed.

According to the invention, the multifunctional organic molecule may be adsorbed on a conducting semiconductor surface or on an insulating surface of a dielectric material. The conducting semiconductor surface contains a semiconductor selected from a III–V and a II–VI material, or mixtures thereof, wherein III, V, II and VI denote the Periodic Table elements III=Ga, In; V=As, P; II=Cd, Zn; VI=S, Se, Te, and is preferably n-GaAs or n-(Al,Ga)As, doped for example with Si.

The dielectric material onto which the multifunctional organic molecule may be adsorbed may be silicon oxide, silicon nitride, or an undoped semiconductor selected from a III–V and a II–VI material, or mixtures thereof, wherein III, V, II and VI denote the Periodic Table elements III=Ga, In; V=As, P; II=Cd, Zn; VI=S, Se, Te, and is preferably undoped GaAs.

In one embodiment, a device according to the invention as shown in FIG. 1 may comprise a conducting layer 2 of 4–30 nm of a suitable semiconductor material, needed for current flow, such as n-GaAs or n-(Al,Ga)As. Localization of the current flow in a thin slab, parallel to the surface to be exposed to the molecules, is desirable, for high sensitivity. This is achieved by having an insulating (near)surface layer, provided by depletion of the electronic carriers due to the surface potential, and by making the conducting layer 2 very thin. A mechanical support is needed for such a very thin layer and is best provided by an insulating undoped semiconductor substrate 1, preferably undoped GaAs. The two electrical contacts are provided, for example, by two AuGeNi electrodes.

In another embodiment, an extra thin insulating layer (3–10 nm), preferably made of a material with the same or a lower bandgap than the material used for the conducting layer 2, is added on top of the conducting layer 2 of thickness between 10–200 nm, so that the multifunctional organic molecules adsorb onto said extra layer. In this case current flow will be localized in a region between the electrodes and just inside the conducting layer, near its interface with the extra insulating film. In this case the electrical contacts are deposited on the extra insulating layer and treated in such a way to assure that electrical contact is made with the conducting layer, which is under the insulating layer.

According to a further embodiment, another insulating layer may be added on top of the insulating layer 1, which is of sufficient thickness for mechanical support, prepared by any of the well-established crystal growth techniques, and another thin film of material (5 nm) is grown as an epitaxial layer of high structural perfection on the first, thicker one, and which can be with the same or preferably with higher bandgap.

Figure 2A:
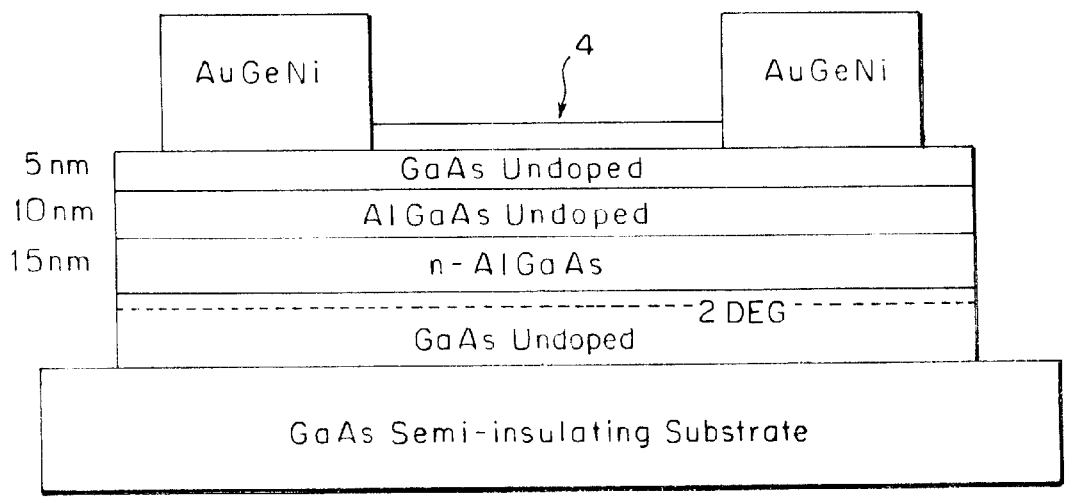
FIG. 2A shows schematically a device according to FIG. 1 that is based on the design of high electron mobility transistors (HEMT's)
Figure 2B:
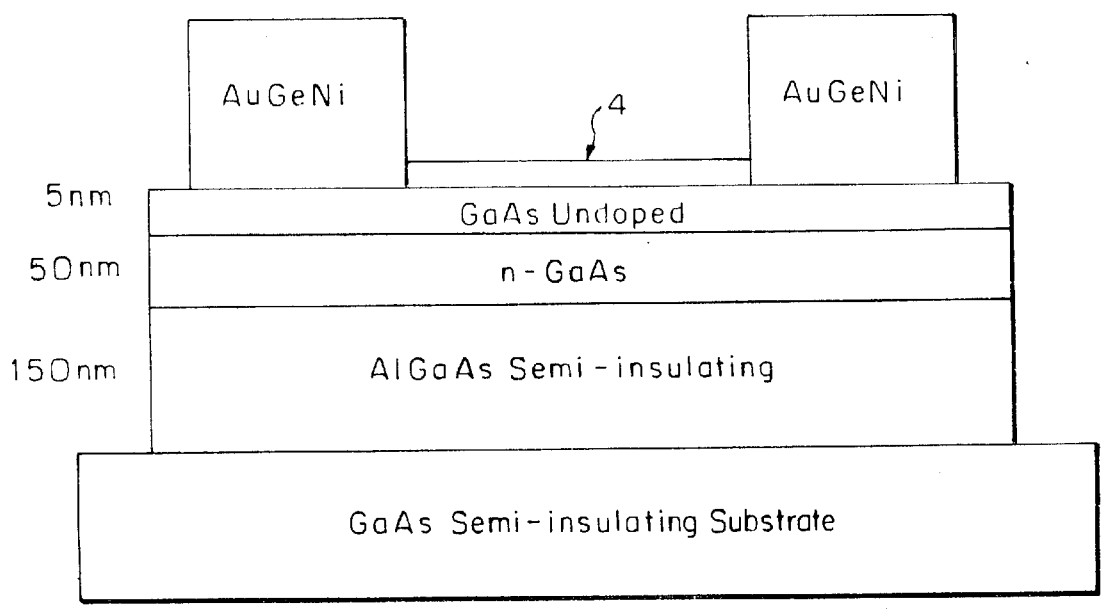
FIG. 2B shows a special version of the device structure depicted in FIG. 1, which is simpler than that shown in FIG. 2A, and is based on a field effect transistor (FET).

FIGS. 2A and 2B shows examples of these two embodiments. FIG. 2A shows a device based on the design of high electron mobility transistors (HEMT), and FIG. 2B shows a simpler device based on the design of field effect transistors (FET). The distance and area between the source and the drain are 2–4 $\mu$m and 6 $\mu$m$^2$, respectively. In both structures, the gate has been replaced by adsorbed multifunctional organic molecules. In the structure of FIG. 2B, the electron density is localized in one dimension, but the electrons have lower mobility than in FIG. 2A because they are located in the doped layer rather than in the less defective undoped one, as is the case with the IEMT-like device of FIG. 2A.

Reference is now made to FIG. 2A, a device structure according to the invention, in which an extra semi-insulating undoped GaAs layer is on top of a semi-insulating GaAs substrate, the idea being that the extra semi-insulating layer can be made to be of higher quality and thus with fewer defects than the bulk substrate. Onto said extra undoped GaAs layer a thin layer (15 nm) of conducting n-(Al,Ga)As is deposited, two further thin layers of undoped (Al,Ga)As (10 nm) and undoped GaAs (5 nm) are deposited on top of the conducting layer, and a thin film 4 of a multifunctional organic molecule is adsorbed on the undoped GaAs surface. This structure serves to create what is called a 2-dimensional electron gas ("2-DEG") just outside the conducting layer. Two AuGeNi electrodes serve as contacts for current flow. The minimum size of the area between the contacts, wherein the multifunctional organic molecules are bound and where the sensing action takes place, depends on the sensitivity of the measurement system and on fabrication limitations. Typically the area will be $\geq 0.2 \mu$m$^2$, with a minimal distance between electrodes of some 100 nm.

Reference is now made to FIG. 2B, which illustrates a FET-like device structure according to the invention in which an extra (Al,Ga)As semi-insulating layer (150 nm) is on top of a GaAs semi-insulating substrate, a thin layer (50 nm) of conducting semiconductor n-GaAs is on top of the semi-insulating (Al,Ga)As layer, a protective upper thin layer of undoped GaAs (5 nm) covers the conducting semiconductor n-GaAs layer, and a thin film 4 of a multifunctional organic molecule is adsorbed on the undoped GaAs surface. Two AuGeNi electrodes serve as electrical contacts. The distance and area between the contacts are at least 0.1 $\mu$m and 0.2 $\mu$m$^2$, respectively.

In all these configurations, an added function of the outermost layer onto which the molecules adsorb, can be to give improved protection against the environment In a preferred embodiment, in a hybrid sensor device according to the invention the electrical current flows preferably at a a distance of no less than 10 nm and not more than 1000 nm from its surface.

In one embodiment, the sensor device changes its conductivity when it is exposed to specific chemicals. In another embodiment, it changes its current as a response to a pulse of light of given wavelength. For example, with porphyrin radicals, the decay time: of the current, following the light pulse, serves for sensing radicals such as $Cu^{2+}$, $CN^-$, $N_3^-$, $NCS^-$ and $NCO^-$, and small molecules such as CO, NO and $H_2O_2$. By means of suitable functional groups other toxic radicals as well as organic and inorganic molecules, including drugs and explosives, can be sensed from a gas phase or from a suitable liquid. The detection is possible by changes induced by the interaction between the molecules bound to the device's surface and the species to be detected. Such changes should affect the surface potential of the area onto which the molecules are adsorbed. This can be due to changes in dipole moment (permanent or induced), changes in charge distribution (in ground or excited state), changes in surface recombination or any combination of these.

According to a further preferred embodiment of the invention, suitable insulating encapsulation for all of the device's exterior except for the area between the electrodes onto which the sensing molecules are bound, can be provided.

Reference is now made to FIGS. 3A–3D which illustrate experiments carried out with devices according to FIGS. 2A and 2B wherein a thin film of the molecules DCDC, DCDS or DMDS is adsorbed on the upper surface of the device. In both cases, the conducting n-(Al,Ga)As and n-GaAs layers of the devices of FIGS. 2A and 2B were doped by Si. The n-(Al,Ga)As layer of FIG. 2A was doped by Si to the concentration of $1.2 \times 10^{18}$ cm$^{-3}$. The n-GaAs layer of FET-like devices of FIG. 2B was doped with two different dopant concentrations, namely $5.0 \times 10^{17}$ cm$^{-3}$ for the low-doped FET-like device and $6.5 \times 10^{17}$ cm$^{-3}$ for the higher conductivity FET-like device, this difference in doping resulting in about three orders of magnitude change in their charge carrier concentrations. Simulations based on the Poisson equation indicate that in these two possible structures of FIG. 2B, the maximum electron density is concentrated at a distance of about 30 to 50 nm from the exposed undoped GaAs upper surface.

In both devices of FIGS. 2A and 2B, the gate has been replaced by adsorbed multifunctional organic molecules that possess two elements: (i) a surface binding element, namely carboxylic acids or cyclic disulfide groups, and (ii) a light-absorbing element of distinct electron affinity. Two families of molecules were synthesized. The first family is derived from tartaric acid which was di-esterified by p-cyanobenzoic acid to provide the corresponding dicarboxylic acid 2,3-di (p-cyanobenzoyl)tartaric acid (DCDC). The second family is based on 1,2-dithiane-4,5-diol which was diesterified by either p-cyanobenzoic acid or p-methoxy-benzoic acid to yield the corresponding disulfides 4,5-dip-cyanobenzoyloxy)-1,2-dithiane (DCDS) and 4,5-di(p-methoxybenzoyloxy)-1,2-dithiane (DMDS), respectively.

The layers of said organic molecules were adsorbed by immersing the devices in a 1 mM solution of the molecules in dry acetonitrile, for periods ranging from 14 hours for DCDC, and up to 72 hours for DCDS and DMDS. FT-IR isotherms showed that under these conditions about one layer of the organic molecules is adsorbed.

Figure 3A:
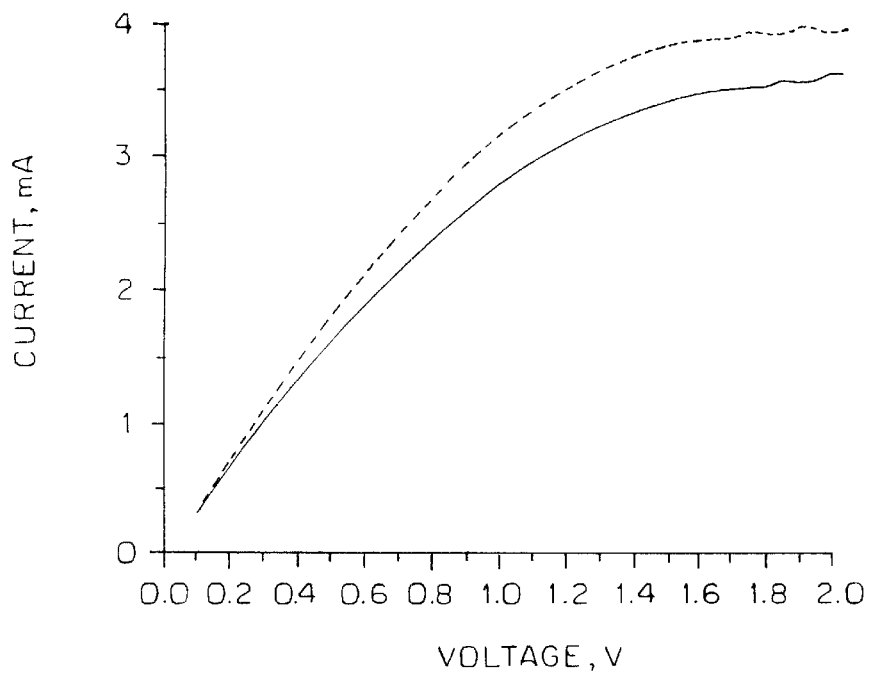
FIGS. 3A–3D show the effect of the adsorbed multifunctional organic sensing molecules 4,5-di(p-cyanobenzoyloxy)-1,2-dithiane (DCDS) (3A), 4,5-di(p-methoxy benzoyloxy)-1,2-dithiane (DMDS) (3B) and 2,3-di(p-cyanobenzoyl)tartaric acid (DCDC) (3C), on the functionality of the solid state HEMT-like structure of FIG. 2A when current (I) versus voltage (V) is applied between the electrical contacts to said structure.
Figure 3B:
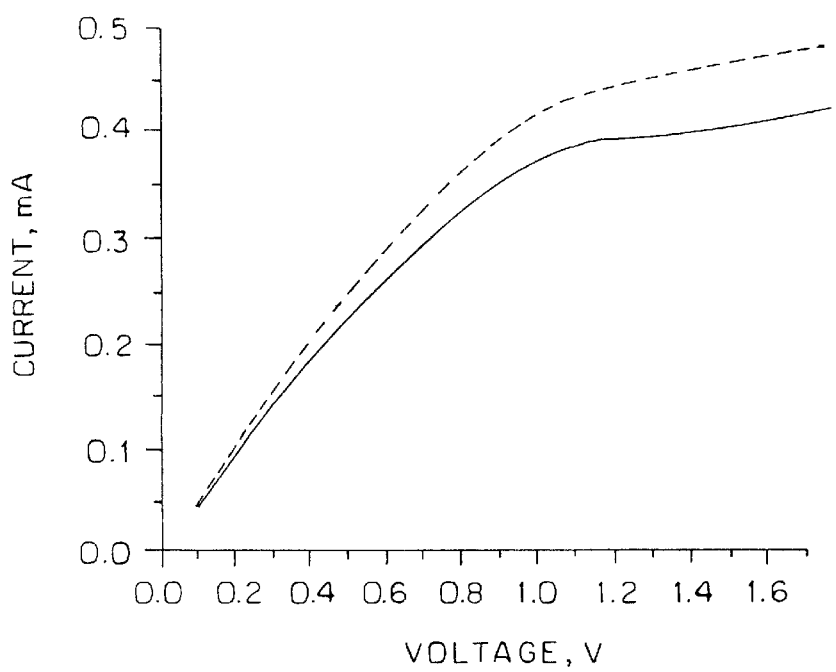
Figure 3C:
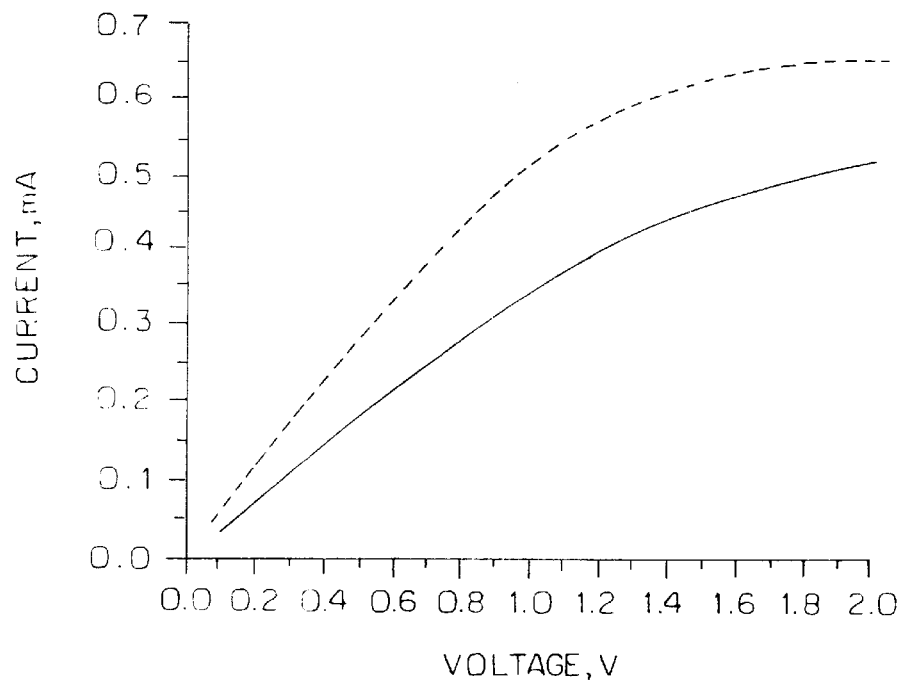
Figure 3D:
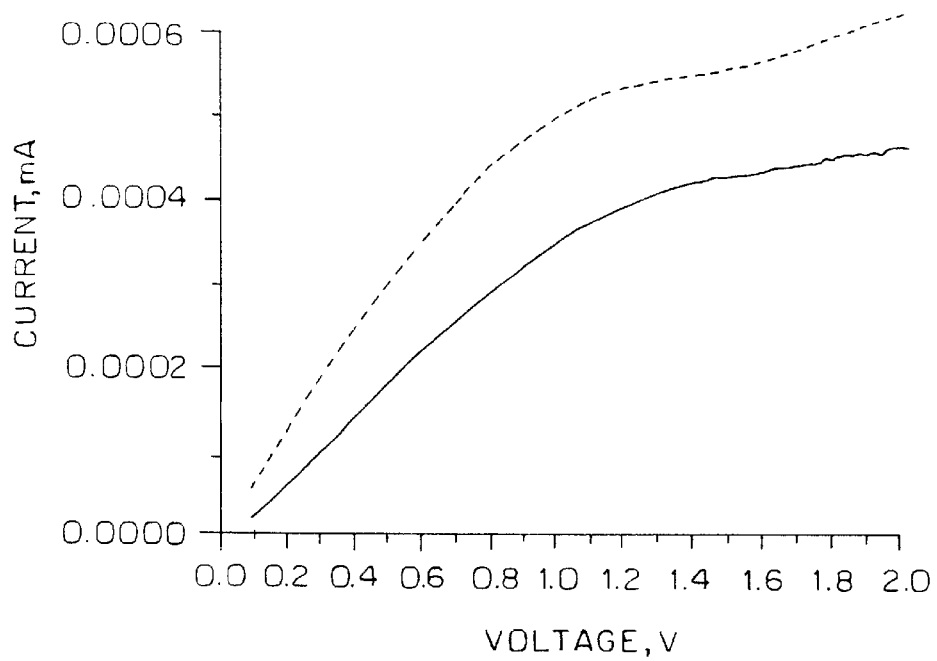

The current-voltage (I/V) characteristics in the ambient between the source and drain with, and without, the adsorbed organic layers, was measured in a HEMT-like device of FIG. 2A (FIGS. 3A–3C) and in the low-doped FET-like device of FIG. 2B (FIG. 3D). In addition, the photocurrent relaxation time was monitored following illumination by a 7 ns pulse-long, tunable (Nd:YAG) pumped dye laser with various wavelength mixing schemes. A constant source-drain voltage of 1.0 V was applied and the current change, following the laser pulse, was monitored. In control experiments devices with a gate, biased negatively with respect to the drain, were examined.

The results are shown in FIGS. 3A–D. The effects induced by the molecules DCDS (FIG. 3A), DMDS (FIG. 3B) and DCDC (FIG. 3C) were found to depend on the doping level of the GaAs. For both the HEMT-like and the FET-like structures with the higher electron concentrations, the molecules affected the current by about 10–20%, depending on the adsorbed molecules. For the lower doped FET-like structure (FIG. 3D), the effect of the DCDC molecules was very dramatic and the current was reduced by an order of magnitude. The reduction in current was more significant for the dicarboxylic acid derivatives than for the disulfide derivatives.

The molecule-induced change in the surface potential could be estimated by comparing the results shown in FIG. 3, with those obtained with a negative bias on the gate of a FET transistor. Applying a bias of 50–100 mV, the reduction in the current between the source and the drain was similar to that obtained upon adsorption of DCDC on the device. However, the effect of the molecules on other electronic properties of the structure cannot be explained simply by the change in surface potential.

Figure 4A:
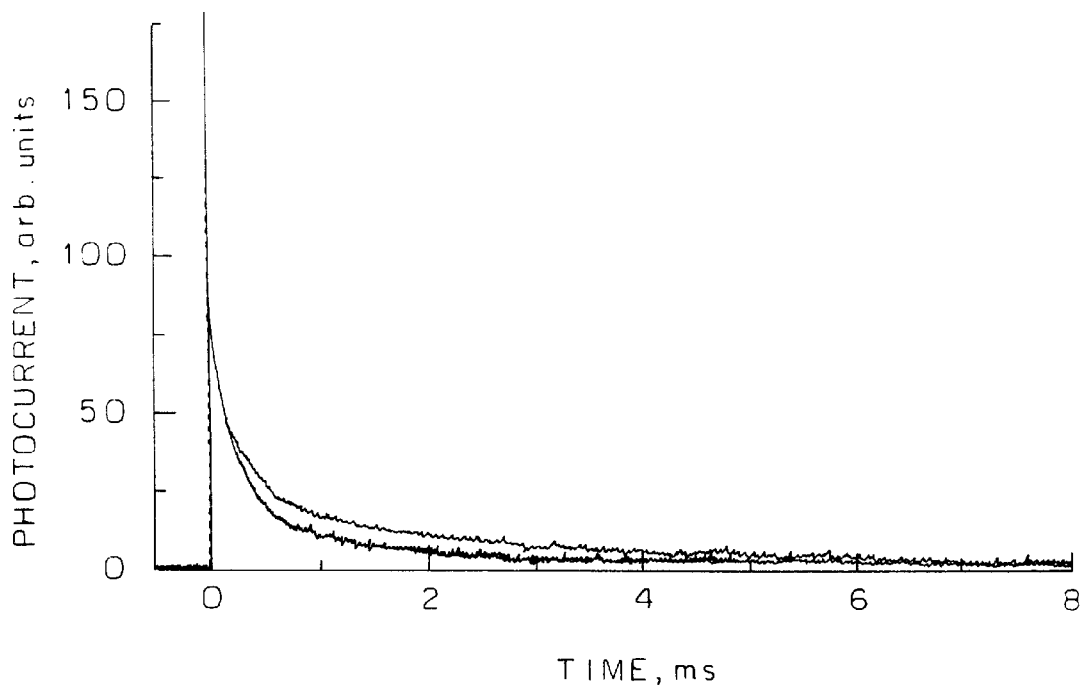
FIGS. 4A–4B show the photocurrent as measured between the two electrodes versus time following exposure of a device shown in FIG. 1B, to a 7 nsec long light pulse of various energies. The device is coated either with 1,2-dithiane-4,5-di(hydroxyquinoline) $Cu^{2+}$ complex or with 1,2-dithiane-4,5-di(hydroxy-quinoline) derivative . The current decay time is shown following excitation at wavelength 266 nm (4A) and 237 nm (4B) for the two molecules.
Figure 4B:
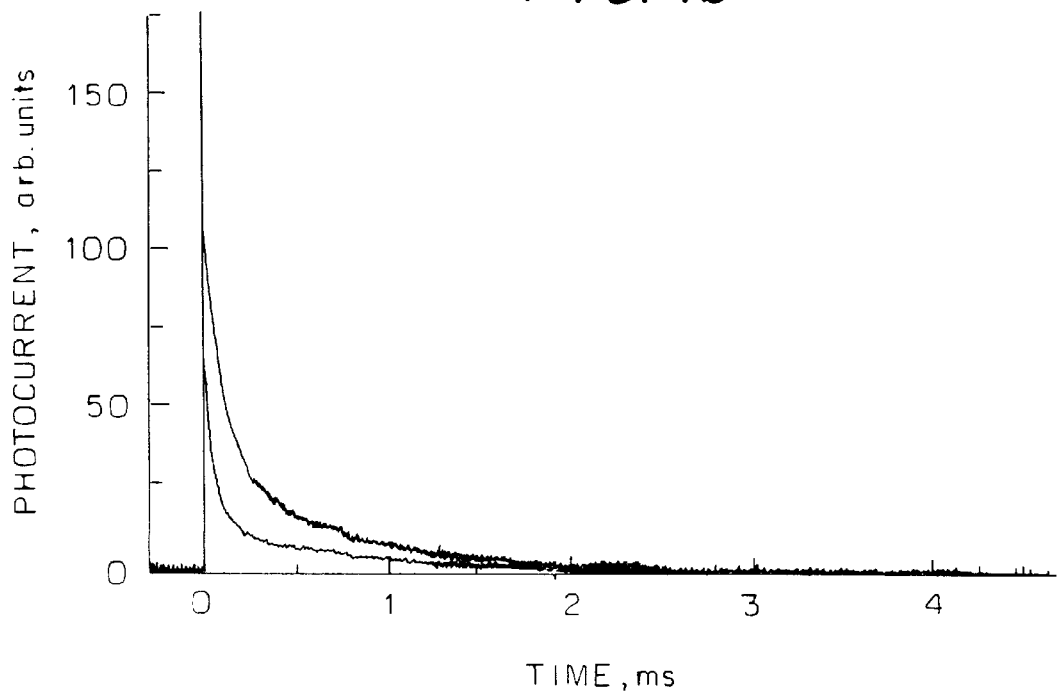
Figure 5A:
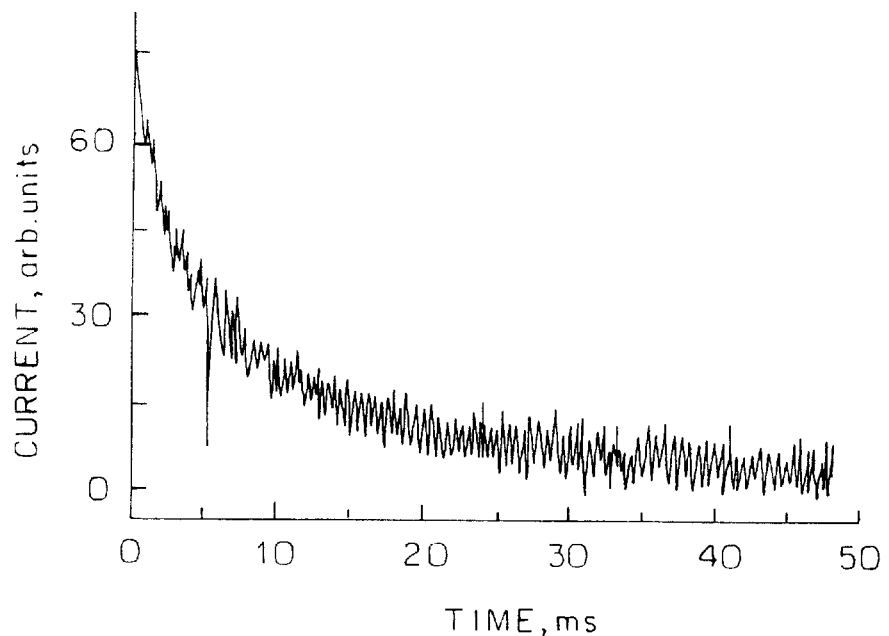
FIGS. 5A–5D show the photocurrent as measured between the two electrodes versus time following exposure of a device shown in FIG. 1A, to a 7 nsec long light pulse of various energies. The device is coated with DCDC. The wavelengths used are 580 nm (5A), 290 nm (5B), 237 nm (5C) and 212 nm (5D) regular intensity—solid line, and high intensity—dotted line. The insert shows the current as measured between the two electrodes versus time following exposure of a bare HEMT-like device to a light pulse of 532 nm (2.33 eV) wavelength.
Figure 5B:
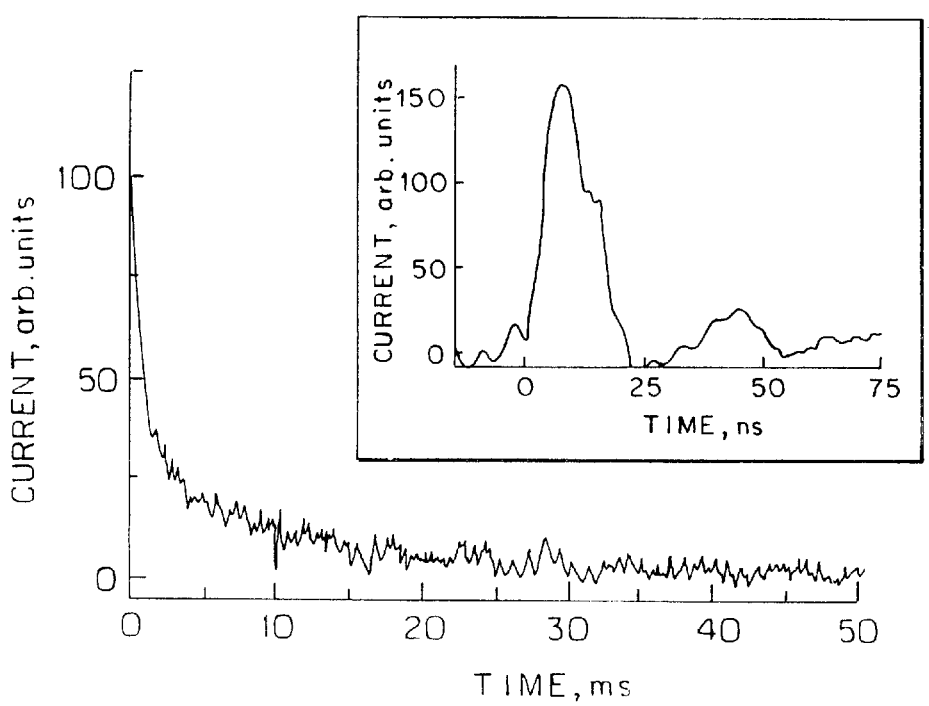
Figure 5C:
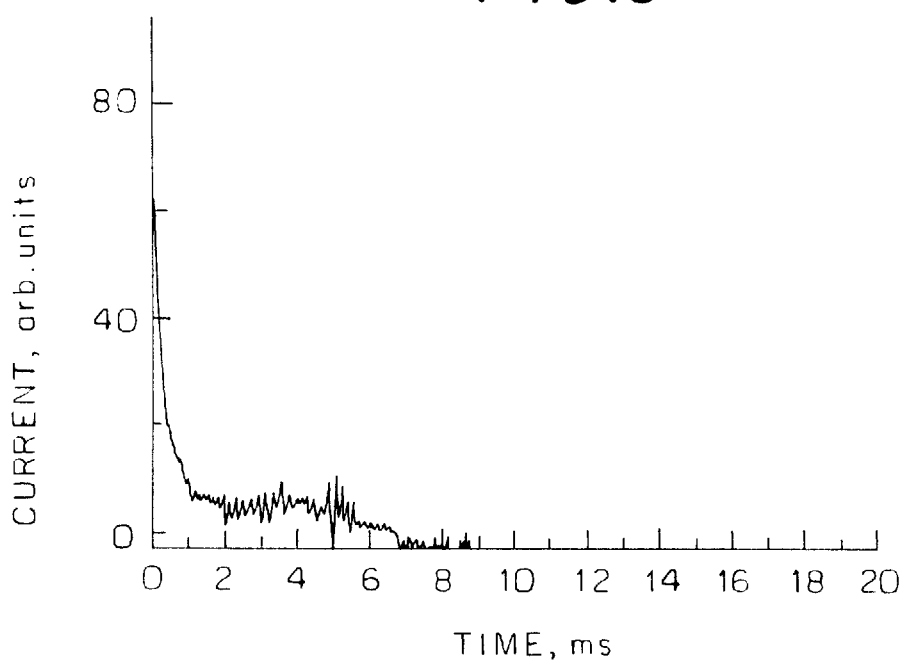
Figure 5D:
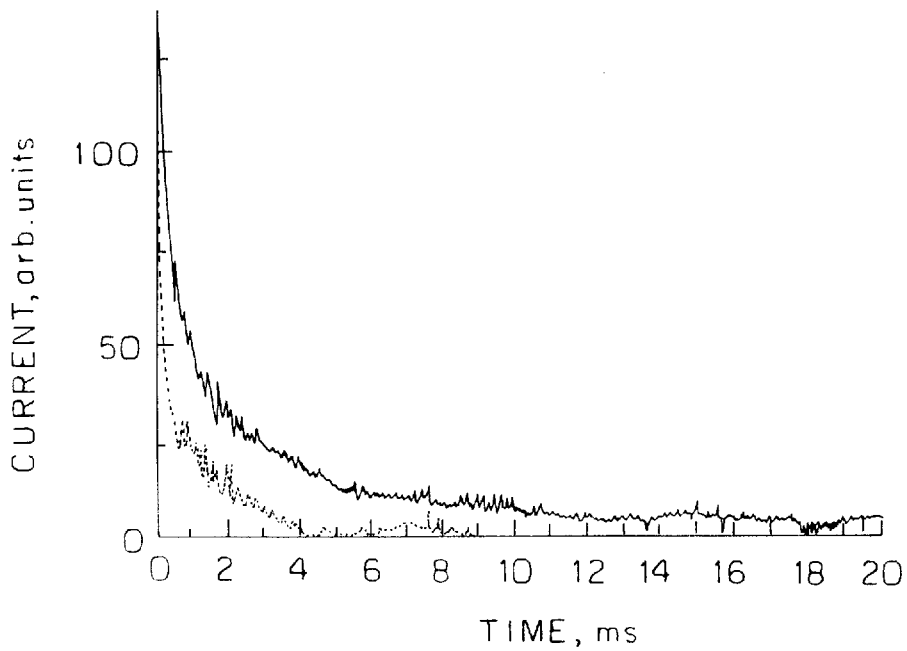

Reference is now made to FIGS. 4A–4B. The results are presented as solid and dashed lines for molecules 1,2-dithiane-4,5-di(hydroxyquinoline) $Cu^+$ complex and 1,2-dithiane-4,5-di(hydroxyquinoline), respectively. While the first molecule has resonance absorption at 237 nm, the second molecule absorbs more strongly at 266 nm. As seen in the figures, when the light pulse coincides with the absorption of the adsorbed molecules, the relaxation time becomes shorter as compared to the case of non-resonant absorption. The time response of the device upon illumination changes drastically when the wavelength of the pulsed illuminating light coincides with the absorption of the adsorbed organic molecules that are adsorbed on its surface. This different time response can serve for detecting specific ions/molecules. In the example in FIG. 4, exposing the device $Cu^+$ solution results in changing the time response of the device at the probed wavelengths.

Light-induced, time-dependent studies were carried out for the HEMT-like device of FIG. 2A. Without the DCDC molecules, photocurrent was measured upon exposure, as shown in the insert in FIG. 5. Upon excitation at a wavelength that corresponds to energy exceeding the band gap (1.4 eV), only a short component of about 20 nsec is observed. This photocurrent results from electron-hole excitation and its relaxation time is consistent with previous photoluminescence measurements (Lunt et al., 1991).

The decay of the photocurrent changed drastically when the DCDC molecules were adsorbed, as shown in FIGS. 5A–5D for a device coated with DCDC and exposed to a laser pulse at various wavelenghts. The decay can be expressed by two additional exponents, $t_1$ and $t_2$. Table 1 summarizes the results presented in FIG. 5 and gives the absorption coefficient of the adsorbed molecule at each wavelength. Both ti and $t_2$ become shorter the better the excitation wavelength matches the absorption band of the adsorbed molecules. Similar results are obtained with the FET-like device, but with slower decays.

TABLE 1

Time constants (t) for photocurrent decay of GaAs/AlGaAs HEMT-like structure, bare and coated with DCDC

| excitation wavelength (nm) | t (nsec) Bare device ± 10% | $t_1$ (msec) +DCDC ± 10% | $t_2$ (msec) +DCDC ± 10% | DCDC absorption coefficient ($\epsilon$) $cm^{-1} M^{-1}$ |
|---|---|---|---|---|
| 580 | 20 | 2.7 | 20.0 | <100 |
| 290 | 20 | 0.8 | 16.0 | 3000 |
| 237 | 20 | 0.2 | 1.6 | 38000 |
| 212 | 20 | 0.4 | 3.4 | 6300 |
| 212 high intensity | 20 | 0.2 | 1.6 | 6300 |

Thus, the above described studies of the interactions between adsorbed organic molecules and the electronic charge carriers in specially made GaAs structures by time and wavelength dependent measurements of the photocurrent, show that adsorption of the molecules modifies the photocurrent decay time by orders of magnitude. The effects are molecularly specific, as they depend on the electronic properties and on the absorption spectrum of the molecules.

The understanding of the electronic interaction between a molecule adsorbed on a semiconductor substrate and the charge carriers in the substrate is a key to achieve suitable combination of predetermined molecular properties with those of solid state electronic devices. According to the present invention, it is shown how one can use structures that are ultra-sensitive to this interaction, how this interaction can be probed by a new method based on time and wavelength dependent studies of the photocurrent, and how the results of such measurements can be used to understand this interaction.

The sensor device of the present invention has several advantages over existing sensors:(i) High sensitivity. The sensitivity of the device does not depend linearly on its surface area, and is defined by the ratio between the number of free charge carriers before the sensor is exposed to light or a chemical to that after it is exposed; (ii) High versatility. Due to the ability to use the same solid state structure with different adsorbed multifunctional organic molecules, the same design principle of the sensor can be used for a variety of applications. The versatility depends only on the ability to synthesize organic molecules with the right specificity and to bind them to the semiconductor surface; (iii) Small dimension. Due to the microelectronics methods used for production of the semiconductor surface and because the sensitivity does not depend linearly on the surface area, very small sensors can be built.

According to the present invention, in contrary to what could be expected by simple extrapolation of existing knowledge and experience, it is shown that it is possible to combine all the four criteria required for good quality of sensors, namely sensitivity, selectivity, robustness, and versatility, in an organic-semiconductor hybrid sensor device which does not have a gate and does not require the junction-type configuration.

The sensor device of the invention has the surprising novel feature that its sensitivity depends supra-linearly on its area. It can be constructed so that small area devices have the same sensitivity as large area ones. It is versatile due to the ability to use tailor-made organic molecules and its robustness stems from the fact that the sensing part of the device, namely the organic molecules, affect the electron flow at a distance away from them, i.e. the sensing element does not pass any current.

Thus, the sensor device of the invention can, due to its special design, high sensitivity and selectivity and small dimensions, serve as a sensor for a large variety of chemicals and as a light detector with wavelength specific sensitivity.

REFERENCES

1. Besser, R. S. and C. R. Helms, 1988, Appl. Phys. Lett., 52, 1707.
2. Bruening, M., E. Moons, D. Cahen, J. Libman, and A. Shanzer, 1994, J. Amer. Chem. Soc. 116, 2972.
3. Bruening, M., E. Moons, D. Cahen, and A. Shanzer, 1995, J. Phys. Chem. 99, 8368
4. Lisensky, G. C., R. L. Penn, C. J. Murphy, and A. B. Ellis, 1990, Science, 248, 840.
5. Lunt, S. R., G. N. Ryba, P. G. Santangelo, and N. S. Lewis, 1991, J. Appl. Phys. 70, 7449.
6. Mandelis, A. and C. Christofides, 1993, "Physics, Chemistry, and Technology of Solid State Gas Sensors Devices", Vol. 125 in "Chemical Analysis", ed. J. D. Winefordner, John Wiley & Sins, Inc., NY.
7. Oh, Y. T. et al., 1994, J. Appl. Phys. 76, 1959.
8. O'Regan, B. and M. Graetzel, 1991, Nature 353, 737.
9. Rickert, J., T. Weiss, and W. Gopel, 1996, Sensors and Actuators B-Chemical, 31, 45.
10. Sandroff, C. J., R. N. Nottenburg, J. C. Bischoff, and R. Bhat, 1987, Appl. Phys. Lett. 51, 33
11. Skromme, B. J., C. J. Sandroff, E. Yablonovitch, and T. Gmitter, 1987, Appl. Phys. Lett. 51, 2022.
12. Yablonovitch, E., C. J. Sandroff, R. Bhat, and T. Gmitter, 1987, Appl. Phys. Lett. 51, 439.

What is claimed is:

1. A hybrid organic-inorganic semiconductor device composed of one or more insulating or semi-insulating layers (1), one conducting semiconductor layer (2), two conducting pads (3), and a layer of multifunctional organic molecules (4), characterized in that:

said conducting semiconductor layer (2) is on top of one of said insulating or semi-insulating layers (1), said two conducting pads (3) are on both sides on top of an upper layer which is either said conducting semiconductor layer (2) or another of said insulating or semi-insulating layers (1), making electrical contact with said conducting semiconductor layer (2), and said layer of multifunctional organic molecules (4) is directly bound through at least one functional group to the surface of said upper layer, between the two conducting pads (3), and at least another of said functional groups of said multifunctional organic molecules binds chemicals or absorbs light, wherein said at least one functional group of said multifunctional organic molecules bound to the surface of said upper layer is selected from the group consisting of one or more aliphatic or aromatic carboxyl, thiol, acyclic sulfide, cyclic disulfide, hydroxamic acid and trichlorosilane groups.

2. A semiconductor device according to claim 1, wherein said conducting semiconductor layer (2) is a layer of a semiconductor selected from the group consisting of a III–V and a II–VI material, or mixtures thereof, wherein III, V, II and VI denote the Periodic Table elements III=Ga, In; V=As, P; II=Cd, Zn; VI=S, Se, Te.

3. A semiconductor device according to claim 2, wherein said conducting semiconductor layer (2) is a layer of doped n-GaAs or doped n-(Al,Ga)As.

4. A semiconductor device according to claim 1, wherein said one or more insulating or semi-insulating layers (1) is selected from the group consisting of silicon oxide, silicon nitride or from an undoped semiconductor selected from the group consisting of a III–V and a II–VI material, or mixtures thereof, wherein III, V, II and VI denote the Periodic Table elements III=Ga, In; V=As, P; II=Cd, Zn; VI=S, Se, Te.

5. A semiconductor device according to claim 4, wherein said undoped semiconductor is undoped GaAs or undoped (Al,Ga)As.

6. A semiconductor device according to claim 1, wherein said conducting semiconductor layer (2) is a layer of doped n-GaAs which is on top of a semi-insulating layer (1) of (Al,Ga)As which is on top of another semi-insulating layer (1) of GaAs, and on top of said conducting semiconductor doped n-GaAs layer (2) there is a semi-insulating undoped GaAs layer (1) to which is bound said layer of multifunctional organic molecules (4).

7. A semiconductor device according to claim 1, wherein said conducting semiconductor layer (2) is a layer of doped n-(Al,Ga)As which is on top of an insulating layer (1) of undoped GaAs which is on top of a semi-insulating layer (1) of GaAs, on top of said conducting semiconductor doped n-(Al,Ga)As layer (2) there is a semi-insulating undoped (Al,Ga)As layer (1) on top of which there is an upper undoped GaAs semi-insulating layer (1), and said layer of multifunctional organic molecules (4) is bound to the upper undoped GaAs semi-insulating layer (1).

8. A semiconductor device according to claim 1, wherein said at least another functional group of said multifunctional organic molecules that binds chemicals is a metal-binding and metal-detecting group selected from the group consisting of radicals derived from hydroxamic acids, bipyridyl, imidazol and hydroxyquinoline.

9. A semiconductor device according to claim 8, wherein said at least another functional group is one which binds and detects a metal ion selected from the group consisting of $Cu^{2+}$, $Fe^{2+}$ and Ru metal ions.

10. A semiconductor device according to claim 1, wherein said at least another function al group of said multifunctional organic molecules that absorbs light is selected from the group consisting of aliphatic or aromatic hydroxamates, substituted aromatic groups, bipyridyl groups, hydroxyquinoline groups, or imidazolyl groups to which a metal porphyrin or a metalphthalocyanin residue is attached.

11. A semiconductor device according to claim 1, wherein said multifunctional organic molecules are selected from the group consisting of 2,3-di(p-cyanobenzoyl) tartaric acid (DCDC), 4,5-di(p-cyano-benzoyloxy)-1,2-dithiane (DCDS), 4,5-di(p-methoxy-benzoyloxy)-1,2-dithiane (DMDS) and 1,2-dithiane-4,5-di(hydroxyquinoline) and the $Cu^{2+}$ complex thereof.

12. In a light or chemical sensor comprising a semiconductor device, the improvement wherein said semiconductor device is a hybrid organic-inorganic semiconductor device according to claim 1.

13. In a light or chemical sensor comprising a semiconductor device, the improvement wherein said semiconductor device is a hybrid organic-inorganic semiconductor device according to claim 2.

14. In a light or chemical sensor comprising a semiconductor device, the improvement wherein said semiconductor device is a hybrid organic-inorganic semiconductor device according to claim 3.

15. In a light or chemical sensor comprising a semiconductor device, the improvement wherein said semiconductor device is a hybrid organic-inorganic semiconductor device according to claim 4.

16. In a light or chemical sensor comprising a semiconductor device, the improvement wherein said semiconductor device is a hybrid organic-inorganic semiconductor device according to claim 6.

17. In a light or chemical sensor comprising a semiconductor device, the improvement wherein said semiconductor device is a hybrid organic-inorganic semiconductor device according to claim 7.

18. In a light or chemical sensor comprising a semiconductor device, the improvement wherein said semiconductor device is a hybrid organic-inorganic semiconductor device according to claim 1.

19. In a light or chemical sensor comprising a semiconductor device, the improvement wherein said semiconductor device is a hybrid organic-inorganic semiconductor device according to claim 8.

20. In a light or chemical sensor comprising a semiconductor device, the improvement wherein said semiconductor device is a hybrid organic-inorganic semiconductor device according to claim 9.

21. In a light or chemical sensor comprising a semiconductor device, the improvement wherein said semiconductor device is a hybrid organic-inorganic semiconductor device according to claim 10.

22. In a light or chemical sensor comprising a semiconductor device, the improvement wherein said semiconductor device is a hybrid organic-inorganic semiconductor device according to claim 11.

23. A method of detecting light or a chemical with a light or chemical sensor, wherein said light or chemical sensor comprises a hybrid organic-inorganic semiconductor device according to claim 1.

24. A semiconductor device according to claim 2, wherein said one or more insulating or semi-insulating layers (1) is selected from the group consisting of silicon oxide, silicon nitride or from an undoped semiconductor selected from the group consisting of a III–V and a II–VI material, or mixtures thereof, wherein III, V, II and VI denote the Periodic Table elements III=Ga, In; V=As, P; II=Cd, Zn; VI=S, Se, Te.

25. A semiconductor device according to claim 24, wherein said multifunctional organic molecules are directly bound to the surface of said upper conducting semiconductor layer (2) or insulating or semi-insulating layer (1), through at least one functional group selected from the group consisting of one or more aliphatic or aromatic carboxyl, thiol, acyclic sulfide, cyclic disulfide, hydroxamic acid and trichlorosilane groups.

26. A semiconductor device according to claim 2, wherein said multifunctional organic molecules are directly bound to the surface of said upper conducting semiconductor layer (2) or insulating or semi-insulating layer (1), through at least one functional group selected from the group consisting of one or more aliphatic or aromatic carboxyl, thiol, acyclic sulfide, cyclic disulfide, hydroxamic acid and trichlorosilane groups.

27. A semiconductor device according to claim 4, wherein said multifunctional organic molecules are directly bound to the surface of said upper conducting semiconductor layer (2) or insulating or semi-insulating layer (1), through at least one functional group selected from the group consisting of one or more aliphatic or aromatic carboxyl, thiol, acyclic sulfide, cyclic disulfide, hydroxamic acid and trichlorosilane groups.

28. A semiconductor device according to claim 6, wherein said multifunctional organic molecules are directly bound to the surface of said upper conducting semiconductor layer (2) or insulating or semi-insulating layer (1), through at least one functional group selected from the group consisting of one or more aliphatic or aromatic carboxyl, thiol, acyclic sulfide, cyclic disulfide, hydroxamic acid and trichlorosilane groups.

29. A semiconductor device according to claim 7, wherein said multifunctional organic molecules are directly bound to the surface of said upper conducting semiconductor layer (2) or insulating or semi-insulating layer (1), through at least one functional group selected from the group consisting of one or more aliphatic or aromatic carboxyl, thiol, acyclic sulfide, cyclic disulfide, hydroxamic acid and trichlorosilane groups.

30. A semiconductor device according to claim 2, wherein said at least another functional group of said multifunctional organic molecules that binds chemicals is a metal-binding and metal-detecting group selected from radicals derived from hydroxamic acids, bipyridyl, imidazol or hydroxyquinoline.

31. A semiconductor device according to claim 4, wherein said at least another functional group of said multifunctional organic molecules that binds chemicals is a metal-binding and metal-detecting group selected from radicals derived from hydroxamic acids, bipyridyl, imidazol or hydroxyquinoline.

32. A hybrid organic-inorganic semiconductor device composed of one or more insulating or semi-insulating layers (1), one conducting semiconductor layer (2), two conducting pads (3), and a layer of multifunctional organic molecules (4), characterized in that:

said conducting semiconductor layer (2) is on top of one of said insulating or semi-insulating layers (1), said two conducting pads (3) are on both sides on top of an upper layer which is either said conducting semiconductor layer (2) or another of said insulating or semi-insulating layers (1), making electrical contact with said conducting semiconductor layer (2), and said layer of multifunctional organic molecules (4) is directly bound through at least one functional group to the surface of said upper layer, between the two conducting pads (3), and at least another of said functional groups of said multifunctional organic molecules binds chemicals or absorbs light, wherein said at least another functional group of said multifunctional organic molecules that binds chemicals is a metal-binding and metal-detecting group selected from the group consisting of radicals derived from hydroxamic acids, bipyridyl, imidazol and hydroxyquinoline.

33. A semiconductor device according to claim 32, wherein said multifunctional organic molecules are selected from the group consisting of 2,3-di(p-cyanobenzoyl) tartaric acid (DCDC), 4,5-di(p-cyano-benzoyloxy)-1,2-dithiane (DCDS), 4,5-di(p-methoxy-benzoyloxy)-1,2-dithiane (DMDS) and 1,2-dithiane-4,5-di(hydroxyquinoline) and the $Cu^{2+}$ complex thereof.

34. A hybrid organic-inorganic semiconductor device composed of one or more insulating or semi-insulating layers (1), one conducting semiconductor layer (2), two conducting pads (3), and a layer of multifunctional organic molecules (4), characterized in that:

said conducting semiconductor layer (2) is on top of one of said insulating or semi-insulating layers (1), said two conducting pads (3) are on both sides on top of an upper layer which is either said conducting semiconductor layer (2) or another of said insulating or semi-insulating layers (1), making electrical contact with said conducting semiconductor layer (2), and said layer of multifunctional organic molecules (4) is directly bound through at least one functional group to the surface of said upper layer, between the two conducting pads (3), and at least another of said functional groups of said multifunctional organic molecules binds chemicals or absorbs light, wherein said at least another functional group of said multifunctional organic molecules that absorbs light is selected from the group consisting of aliphatic or aromatic hydroxamates, substituted aromatic groups, bipyridyl groups, hydroxyquinoline groups, or imidazolyl groups to which a metal porphyrin or a metal-phthalocyanin residue is attached.

35. A semiconductor device according to claim 34, wherein said multifunctional organic molecules are selected from the group consisting of 2,3- di(p-cyanobenzoyl) tartaric acid (DCDC), 4,5-di(p-cyano-benzoyloxy)-1,2-dithiane (DCDS), 4,5-di(p-methoxy-benzoyloxy)-1,2-dithiane (DMDS) and 1,2-dithiane-4,5-di(hydroxyquinoline) and the $Cu^{2+}$ complex thereof.

* * * * *